United States Patent [19]

de Framond

[11] Patent Number: 6,018,099
[45] Date of Patent: Jan. 25, 2000

[54] TISSUE-PREFERENTIAL PROMOTERS

[75] Inventor: Annick J. de Framond, Durham, N.C.

[73] Assignee: Novartis Finance Corporation, New York, N.Y.

[21] Appl. No.: 08/450,653

[22] Filed: May 25, 1995

Related U.S. Application Data

[62] Division of application No. 08/322,962, Oct. 13, 1994, Pat. No. 5,466,785, which is a continuation of application No. 08/071,209, Jun. 2, 1993, abandoned, which is a continuation of application No. 07/508,207, Apr. 12, 1990, abandoned.

[51] Int. Cl.[7] .......................... H01H 5/00; C12N 15/05; C12N 15/32
[52] U.S. Cl. .................. 800/205; 435/172.3; 435/172.1; 47/58; 47/DIG. 2; 536/23.1; 536/23.6; 536/24.1; 935/6; 935/22; 935/23; 935/67; 935/30
[58] Field of Search ..................................... 800/205, 200, 800/250, DIG. 56; 435/172.3, 172.1; 47/58; 536/23.1, 236, 24.1, 23.71; 935/6, 22, 23, 67, 30

[56] References Cited

U.S. PATENT DOCUMENTS

| | | | |
|---|---|---|---|
| 4,940,661 | 7/1990 | Etcheverry et al. | 435/69.1 |
| 5,023,179 | 6/1991 | Lam et al. | 435/172.3 |
| 5,550,318 | 8/1996 | Adams et al. | 800/205 |

OTHER PUBLICATIONS

"Keystone Crops" Agricultural Genetics Report, Mar. 1990.
Awad et al., "Prescence of a metallothionein–lke protein in the bovine pineal gland", *Journal of Neural Transmission*, 76:129–144 (1989).
Baer et al., "Influence of Capture Stress, Salinity and Reproductive Status on Zinc Associated with Metallothionein–Like Proteins in the Livers of Three Marine Teleost Species", *Marine Envirnoment Research*, 29:277–287 (1990).
Barker et al., "Cellular localization of soybean storage protein mRNA in transformed tobacco seeds", *PNAS USA*, 85:458–462 (1988).
Barton, K.A., et al., "*Bacillus thuringiensis* δ–Endotoxin Expressed in Transgenic *Nicotiana Tabacum* Provides Resistance to Lepidopteran Insects", *Plant Physiol.*, 85:1103–1109 (1987).
Benfey et al., "Regulated Genes in Transgenic Plants", *Science*, 244:174–181 (1989).
Colot et al., "Localization of sequences in wheat endorsperm protein genes which confer tissue–specific expression in tobacco", *EMBO*, 6(12):3559–3564 (1987).
Conkling, M.A., et al., "Isolation of Transcriptionally Regulated Root–Specific Genes from Tobacco", *Plant Physiol.*, 93:1203–1211 (1990).
de Framond et al., "Cloning and Characterization of a Maize Metallothionein Gene", *J. Cell. Biochem.*, UCLA Sympos Abstract R211, p. 298 (1990).
de Miranda et al., "Metallothionein genes from the flowering Plant *Mimulus guttatus*", *FEBS Letters*, 260(2):227–280 (1990).

Evans, I.M., et al., "Distribution of Root mRNA Species in other Vegetative Organs of pean (*Pisum Sativum* L.)", *Mol. Gen. Genet.*, 214:153–157 (1988).
Evans, et al., "A gene from pean (*Pisum Sativum* :L.) with homology to metallothionein genes", 262(1):29–32 (1990).
Fischhoff, D.A., et al., "Insect Tolerant Transgenic Tomato Plants", *Bio/Technology*, 5:807–813 (1987).
Fluhr et al., "Organ–Specific and Light–Induced Expression of Plant Genes", *Science*, 232:1106–1112 (1986).
Lam et al., "ASF–2: A Factor That Binds to the Cauliflower Mosaic Virus 35S Promoter and a Conserved GATA Motif in Cab Promoters", *The Plant Cell*, 1:1147–1156 (1989).
Lam et al., "Site–Specific mutations alter in vitro factor bindng and change promoter expression pattern in transgenic plants", *PNAS USA*, 86:7890–7894 (1989).
Lerner, D., et al., "Cloning and Characterization of Root–Specific Farley Lectin[1]", *Plant Physiol.*, 91:124–129 (1989).
O'Connell, et al., "Somatic hybridization between *Lycopersicon esculentum* and *Lycopersicon pennellii*", *TAG*, 70:1–12 (1985).
Palmiter, *Matallothionein II*, 63–80 (ed. Kagi et al. Birkhauser, Verlag, Basel 1987).
Perlak, F.J., et al., "Genetically Improved Potatoes: Protection from Damage by Colorado Potato Beetles", *Plant Molecular Biology*, 22:313–321 (1993).
Reeck et al., "Homology" in Proteins and Nucleic Acids: A Terminology Muddle and a way out of it, *Cell*, 50:667 (1987).
Rauser et al., "Cadmium–binding protein in roots of maize", *Can. J. Bol.*, 62:1645–1650 (1984).
Scherntaner, J.P., et al., "Endosperm–specific Activity of a Zein Gene Promoter in Transgenic Tobacco Plants", *The EMBO Journal*, 8(2):343–350 (1989).
Slice, L.W., et al., "Purification, Characterization, and cDNA Cloning of a Novel Metallothionein–like, Cadmium–binding Protein from *Caenorhabditis elegans*", *Journal of Biological Chemistry*, 265(1):256–263 (1990).
Stiefel et al., "Molecular cloning of cDNAs encoding a putative cell wall protein from *Zea mays* and immunological identification of related polypeptides", *Plant Molecular Biology*, 11:483–493 (1988).
Stinson et al., "Genes Expressed in the Male Gametophyte of Flowering Plants and Their Isolation", *Plant Physiology*, 83:442–447 (1987).
Teeri, T.H., et al., "Gene Fusions to lacZ Reveal New Expression Patterns of Chimeric Genes in Transgenic Plants", *The EMBO Journal*, 8(2):343–350 (1989).
Vaeck, M., et al., "Transgenic Plants Protected from Insect Attack", *Nature*, 328:33–37 (1987).
Yamanoto et al., "A Tobacco Root–Specific Gene: Characterization and Regulation of its Expression", *J. Cell. Biochem.*, UCLA Symposia, Abstract M352 p. 313 (1989).
Yamamoto et al., A Tobacco Root–Specific Gene; Characterization and Regulation of its Transcription (Thesis, North Carolina Stae University Genetics Department (1989).

*Primary Examiner*—Gary Benzion
*Attorney, Agent, or Firm*—J. Timothy Meigs; Gary M. Pace

[57] ABSTRACT

DNA sequences are able to function as promoters of tissue-preferential transcription of associated DNA sequences in plants, particularly in the roots. These DNA sequences can be used in transformation vectors to produce transgenic plants which will express the heterologous genes preferentially in tissue, particularly in the roots of maize plants.

7 Claims, 13 Drawing Sheets

```
   1 ATTCTTCAAGAGATCGAGCTTCTTTTGCACCACAAGGTCGAGG ATG TCTT  50
     ||||||||||||||||||||||||||||||||||||||||||| ||| ||||
2522 ATTCTTCAAGAGATCGAGCTTCTTTTGCACCACAAGGTCGAGG ATG TCTT 2571

51 GCAGCTGCGGATCAAGCTGCGGCTGCGGCTCAAGCTGCAAGtGCG.....  95
     |||||||||||||||||||||||||||||||||||||||||| |||
2572 GCAGCTGCGGATCAAGCTGCGGCTGCGGCTCAAGCTGCAAGTGCGGGTAA 2621

175 bp  :  intron

96 ....................GCAAGAAGTACCCTGACCTGGAGGAGACG 124
                         |||||||||||||||||||||||||||||
2772 ATTTGCGCGCTGTCCTTTTCAGCAAGAAGTACCCTGACCTGGAGGAGACG 2821

125 AGCACCGCCGCGCAGCCCACCGTCGTCCTCGGGGTGGCCCCGGAGAAGAA 174
     ||||||||||||||||||||||||||||||||||||||||||||||||||
2822 AGCACCGCCGCGCAGCCCACCGTCGTCCTCGGGGTGGCCCCGGAGAAGAA 2871

175 GGCCGCGCCCGAGTTCGTCGAGGCCGCGGCGGAGTCCGGCGAGGCCGCCC 224
     ||||||||||||||||||||||||||||||||||||||||||||||||||
2872 GGCCGCGCCCGAGTTCGTCGAGGCCGCGGCGGAGTCCGGCGAGGCCGCCC 2921

225 ACGGCTGCAGCTGCGGTAGCGGCTGCAAGTGCGACCCCTGCAACTGCTGA 274
     ||||||||||||||||||||||||||||||||||||||||||||||||||
2922 ACGGCTGCAGCTGCGGTAGCGGCTGCAAGTGCGACCCCTGCAACTGCTGA 2971

275 TCACATCGATCGACGACCATGGATATGATTATTATCTATCTAGCTTGTGG 324
     ||||||||||||||||||||||||||||||||||||||||||||||||||
2972 TCACATCGATCGACGACCATGGATATGATTATTATCTATCTAGCTTGTGG 3021

325 TGGTGGTTGAACAATAATAAGCGAGGCCGAGCTGGCTGCCATACATAGGT 374
     ||||||||||||||||||||||||||||||||||||||||||||||||||
3022 TGGTGGTTGAACAATAATAAGCGAGGCCGAGCTGGCTGCCATACATAGGT 3071

375 ATTGTGTGGTGTGTGTGTGAGAGAGAGAGAAACAGAGTTCTTCAGTTTGC 424
     ||||||||||||||||||||||||||||||||||||||||||||||||||
3072 ATTGTGTGGTGTGTGTGTGAGAGAGAGAGAAACAGAGTTCTTCAGTTTGC 3121

425 TATCTCTCTCTGCATGTTTGGCGTCAGTCTTTGTGCTCATGTACGTGTGT 474
     ||||||||||||||||||||||||||||||||||||||||||||||||||
3122 TATCTCTCTCTGCATGTTTGGCGTCAGTCTTTGTGCTCATGTACGTGTGT 3171

475 CTACATGCATGTTGGTTGATCCGATTGCGTCTGCTGTAACCATATATTAA 524
     ||||||||||||||||||||||||||||||||||||||||||||||||||
3172 CTACATGCATGTTGGTTGATCCGATTGCGTCTGCTGTAACCATATATTAA 3221

525 TTGGTCCACGATGATATGATTTGATACTATATATATACTAAAACCGGA 574
     ||||||||||||||||||||||||||||||||||||||||||||||||
3222 TTGGTCCACGATGATATGATTTGATACTATATATATACTAAAACCGGA 3271

575 CTTATT 580
     ||||||
3272 CTTATT 3277
```

*Fig. 5*

Fig. 6A
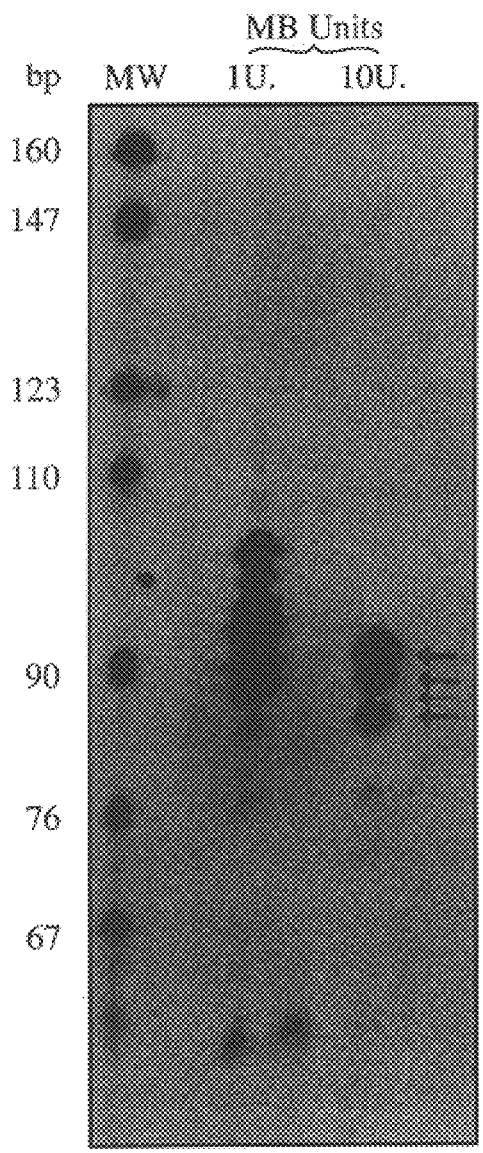
Fig. 6B
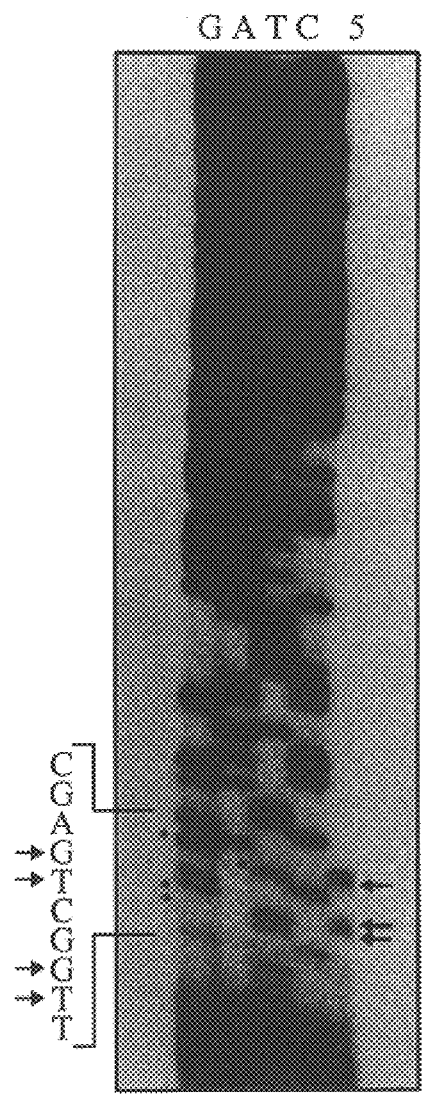
```
  1 TATGGCGTGG TGACACGGCG CGTTGCCCAT ACATCATGCC TCCATCGATG
 51 ATCCATCCTC ACTTGCTATA AAAAGAGGTG TCCATGGTGC TCAAGCTCAG
101 CCAAGCAAAT AAGACGACTT GTTTCATTGA TTCTTCAAGA GATCGAGCTT
151 CTTTTGCACC ACAAGGTCGA GGATGTCTTG CAG
```
Fig. 6C

Fig. 7A

```
Corn  1  MS.CSCGSSCGCGSSCKCGKKYPDLEETSTAAQPTVVLGVAPEKKAAPEF  49
         || | |||||| || |||| |   |       || ||| | |        |
Pea   1  MSGCGCGSSCNCGDSCKCNKRSSGLSYSEMETTETVILGVGPAK...IQF  47

Corn  50 VEAAAESGEAAHGCSCGSGCKCDPCNC.  77
         |               || ||  | ||||||
Pea   48 EGAEMSAASEDGGCKCGDNCTCDPCNCK  76
```

Fig. 7B

| | |
|---|---|
| Corn | S C S C G S S C G C G S S C K C |
| Pea | S G C G C G S S C N C G D S C K C |
| Equine MT-1A | C S C P T G G S C T C A G S C K C |
| N. crassa | C G C S G A S S C N C G S G C S C |

Fig. 7C

| | |
|---|---|
| Corn | C S C G S G C K C D P C N C |
| Pea | C K C G D N C T C D P C N C |
| Equine MT-1A | C T C A G S C K C K E C R C |
| N. crassa | C N C G S G C S C S N C G S |

Fig. 9A
Tissue Preferential Promoter DNA Sequence

```
   1  AAGCTTGCAC ATGACAACAA TTGTAAGAGG ATGGAGACCA CAACGATCCA
  51  ACAATACTTC TGCGACGGGC TGTGAAGTAT AGAGAAGTTA AACGCCCAAA
 101  AGCCATTGTG TTTGGAATTT TTAGTTATTC TATTTTTCAT GATGTATCTT
 151  CCTCTAACAT GCCTTAATTT GCAAATTTGG TATAACTACT GATTGAAAAT
 201  ATATGTATGT AAAAAAATAC TAAGCATATT TGTGAAGCTA AACATGATGT
 251  TATTTAAGAA AATATGTTGT TAACAGAATA AGATTAATAT CGAAATGGAA
 301  ACATCTGTAA ATTAGAATCA TCTTACAAGC TAAGAGATGT TCACGCTTTG
 351  AGAAACTTCT TCAGATCATG ACCGTAGAAG TAGCTCTCCA AGACTCAACG
 401  AAGGCTGCTG CAAGGCCACA AATGCATGAC ATGCATCCTT GTAACCGTCG
 451  TCGCCGCTAT AAACACGGAT AACTCAATTC CCTGCTCCGT CAATTTAGAA
 501  ATGAGCAAGC AAGCACCCGA TCGCTCACCC CATATGCGCC AATCTGACTC
 551  CCAAGTCTCT GTTTCGCATT AGTACCGCCA GCACTCCACC TATAGCTACC
 601  AATTGAGACC TTTCCAGCCT AAGCAGATCG ATTGATCGTT AGAGTCAAAG
 651  AGTTGGTGGT ACGGGTACTT TAACTACCAT GGAATGATGG GGCGTGATGT
 701  AGAGCGGAAA GCGCCTCCCT ACGCGGAACA ACACCCTCGC CATGCCGCTC
 751  GACTACAGCC TCCTCCTCGT CGGCCGCCCA CAACGAGGGA GCCCGTGGTC
 801  GCAGCCACCG ACCAGCATGT CTCTGTGTCC TCGTCCGACC TCGACATGTC
 851  ATGGCAAACA GTCGGACGCC AGCACCAGAC TGACGACATG AGTCTCTGAA
 901  GAGCCCGCCA CCTAGAAAGA TCCGAGCCCT GCTGCTGGTA GTGGTAACCA
 951  TTTTCGTCGC GCTGACGCGG AGAGCGAGAG GCCAGAAATT TATAGCGACT
1001  GACGCTGTGG CAGGCACGCT ATCGGAGGTT ACGACGTGGC GGGTCACTCG
1051  ACGCGGAGTT CACAGGTCCT ATCCTTGCAT CGCTCGGGCC GGAGTTTACG
1101  GGACTTATCC TTACGACGTG CTCTAAGGTT GCGATAACGG GCGGAGGAAG
1151  GCGTGTGGCG TGCGGAGACG GTTTATACAC GTAGTGTGCG GGAGTGTGTT
1201  TCGTAGACGC GGGAAAGCAC GACGACTTAC GAAGGTTAGT GGAGGAGGAG
1251  GACACACTAA AATCAGGACG CAAGAAACTC TTCTATTATA GTAGTAGAGA
```

Fig. 9B

```
1301  AGAGATTATA GGAGTGTGGG TTGATTCTAA AGAAAATCGA CGCAGGACAA
1351  CCGTCAAAAC GGGTGCTTTA ATATAGTAGA TATATATATA TAGAGAGAGA
1401  GAGAAAGTAC AAAGGATGCA TTTGTGTCTG CATATGATCG GAGTATTACT
1451  AACGGCCGTC GTAAGAAGGT CCATCATGCG TGGAGCGAGC CCATTTGGTT
1501  GGTTGTCAGG CCGCAGTTAA GGCCTCCATA TATGATTGTC GTCGGGCCCA
1551  TAACAGCATC TCCTCCACCA GTTATTGTA AGAATAAATT AAGTAGAGAT
1601  ATTTGTCGTC GGGCAGAAGA AACTTGGACA AGAAGAAGAA GCAAGCTAGG
1651  CCAATTTCTT GCCGGCAAGA GGAAGATAGT GGCCTCTAGT TTATATATCG
1701  GCGTGATGAT GATGCTCCTA GCTAGAAATG AGAGAAGAAA AACGGACGCG
1751  TGTTTGGTGT GTGTCAATGG CGTCCATCCT TCCATCAGAT CAGAACGATG
1801  AAAAAGTCAA GCACGGCATG CATAGTATAT GTATAGCTTG TTTTAGTGTG
1851  GCTTTGCTGA GACGAATGAA AGCAACGGCG GCATATTTT TCAGTGGCTG
1901  TAGCTTTCAG GCTGAAAGAG ACGTGGCATG CAATAATTCA GGGAATTCGT
1951  CAGCCAATTG AGGTAGCTAG TCAACTTGTA CATTGGTGCG AGCAATTTTC
2001  CGCACTCAGG AGGGCTAGTT TGAGAGTCCA AAAACTATAG GAGATTAAAG
2051  AGGCTAAAAT CCTCTCCTTA TTTAATTTTA AATAAGTAGT GTATTTGTAT
2101  TTTAACTCCT CCAACCCTTC CGATTTATG GCTCTCAAAC TAGCATTCAG
2151  TCTAATGCAT GCATGCTTGG CTAGAGGTCG TATGGGGTTG TTAATAGCAT
2201  AGCTAGCTAC AAGTTAACCG GGTCTTTTAT ATTTAATAAG GACAGGCAAA
2251  GTATTACTTA CAAATAAAGA ATAAAGCTAG GACGAACTCG TGGATTATTA
2301  CTAAATCGAA ATGGACGTAA TATTCCAGGC AAGAATAATT GTTCGATCAG
2351  GAGACAAGTG GGGCATTGGA CCGGTTCTTG CAAGCAAGAG CCTATGGCGT
2401  GGTGACACGG CGCGTTGCCC ATACATCATG CCTCCATCGA TGATCCATCC
2451  TCACTTGCTA TAAAAGAGG TGTCCATGGT GCTCAAGCTC AGCCAAGCAA
2501  ATAAGACGAC TTGTTTCATT GATTCTTCAA GAGATCGAGC TTCTTTTGCA
2551  CCACAAGGTC GAGGATGTCT TGCAGCTGCG GATCAAGCTG CGGCTGCGGC
2601  TCAAGCTGCA AGTGCGGGTA ATATATAATA ATATATAAGT GCACCGTGCA
```

Fig. 9C

```
2651  TGATTAATTT CTCCAGCCTT CTTCTTGTCT TGTCTAGTTA ATTTCCCTTC
2701  TTTATTTATT TTTTCCATTG CAAAACAAAC AAACAAAAAA CAAAGTTAAT
2751  CTGGATCGAG TAGTTCAATC CATTTGCGCG CTGTCCTTTT CAGCAAGAAG
2801  TACCCTGACC TGGAGGAGAC GAGCACCGCC GCGCAGCCCA CCGTCGTCCT
2851  CGGGGTGGCC CCGGAGAAGA AGGCCGCGCC CGAGTTCGTC GAGGCCGCGG
2901  CGGAGTCCGG CGAGGCCGCC CACGGCTGCA GCTGCGGTAG CGGCTGCAAG
2951  TGCGACCCCT GCAACTGCTG ATCACATCGA TCGACGACCA TGGATATGAT
3001  TATTATCTAT CTAGCTTGTG GTGGTGGTTG AACAATAATA AGCGAGGCCG
3051  AGCTGGCTGC CATACATAGG TATTGTGTGG TGTGTGTGTG AGAGAGAGAG
3101  AAACAGAGTT CTTCAGTTTG CTATCTCTCT CTGCATGTTT GGCGTCAGTC
3151  TTTGTGCTCA TGTACGTGTG TCTACATGCA TGTTGGTTGA TCCGATTGCG
3201  TCTGCTGTAA CCATATATTA ATTGGTCCAC GATGATATGA TTTGATACTA
3251  TATATATATA CTAAAACCGG ACTTATTATA ATACTTGTAG TATATAAGTT
3301  TCTTACGCCC GCAATTGATC GATTCAGAAC GAAGGAGTTC TAGCTAGCTA
3351  AAACATGCAG ATTCAGAATA TCAGATTTTA CGACTACTGG AGGACAAGAA
3401  TAT
```

TISSUE-PREFERENTIAL PROMOTERS

This is a divisional application of Ser. No. 08/322,962, filed Oct. 13, 1994, now U.S. Pat. No. 5,466,785, which is a continuation of Ser. No. 08/071,209, filed Jun. 2, 1993 now abandoned which is a continuation of Ser. No. 07/508,207 filed Apr. 12, 1990, now abandoned.

FIELD OF THE INVENTION

This invention relates to novel DNA sequences which function as promoters of tissue-preferential transcription of associated DNA sequences. More specifically, this invention relates to novel promoters which direct the transcription of associated DNA sequences preferentially in roots, stems and leaves of a plant, most preferably in the roots of maize plants.

BACKGROUND OF THE INVENTION

Transcription of many plant genes is controlled in a temporal and spatial manner. The regulation of gene activity is mediated by the interaction of trans acting factors and cis regulatory elements in the promoter region of a gene. Recent work has elucidated the working of light-regulated genes in plants as well as organ-specific expression and developmentally controlled abundant gene products such as seed storage proteins. Benfey et al., *Science* 244: 174–181 (1989). For example, Barker et al., *PNAS(USA)* 85: 458–462 (1988) have transformed a gene encoding a major seed storage protein from soybean into tobacco and have shown the protein to be expressed in the proper temporal and developmental patterns. Fluhr et al., *Science* 232: 1106–1112 (1986) showed a 5'-fragment from a pea rbcS gene to be responsible for leaf-specificity as well as light response in that gene.

Colot et al., *EMBO* 6:3559–3563 (1987) described promoter sequences from wheat endosperm protein genes that direct a tissue-specific expression pattern in transgenic tobacco similar to that seen in wheat.

It has been suggested that promoters may contain several active sub-elements, or domains, that confer some differential expression properties. For example, much work has been done with the cauliflower mosaic virus (CaMV) promoter 35S. Lam et al., *The Plant Cell*, 1: 1147–1156 (1989) have shown that the CaMV 35S promoter consists of at least two domains; Domain A confers preferential expression in roots; Domain B confers preferential expression in leaf. When Domain A was added to the pea rbcS3A promoter, which is a green tissue specific promoter, the resulting construct promoted expression in roots. In seeds, expression from domain A was detected in the radicle of the embryo and expression from domain B was detected primarily in the cotyledons. Lam et al., *PNAS USA*, 86: 7890–7894 (1989) found that the ASF-1 binding site of the CaMV 35S promoter is required for high expression of the 35S promoter in the root.

Inducible gene activity has been studied in various systems and promoter analysis has identified regions involved in the inducible control of gene activity in these systems. One example of a class of inducible genes is the animal metallothionein protein genes. Expression of mammalian metallothionein protein genes are induced by the presence of elevated concentrations of trace metals, hormones and stress. Palmiter, *Metallothionein II*, 63–80 (ed. Kagi et al. Binkhauser, Verlag, Basel 1987). It is also known that various plant genes are inducible by chemical regulators. For example, the production of chitinase is induced by ethylene. Boller et al., *Planta*, 157:22–31 (1983).

Despite their important role in plant development, relatively little work has been done on the regulation of gene expression in roots. Yamamoto, *A Tobacco Root-Specific Gene; Characterization and Regulation of its Transcription*, (Thesis North Carolina State University Genetics Department, 1989), reported the isolation of genes that are expressed at high levels in tobacco roots and undetectable levels in tobacco leaves. 5' flanking regions from one such gene were fused to a reporter gene. Root specific expression of the fusion genes was analyzed in transgenic tobacco. Yamamoto further characterized one of those genes, the TobRB7-5A gene, including the promoter region. Yamamoto theorized that the gene may contain generalized transcriptional enhancers, or additional root-specific elements.

SUMMARY OF THE INVENTION

It is one object of the present invention to provide tissue-preferential and particularly, root-preferential promoters to drive the expression of genes in greater abundance in plant roots than in other tissue of the plant.

It is another object of the present invention to provide vectors for tissue-preferential, and particularly, for root-preferential heterologous expression of genes in plants.

It is a further object of the present invention to provide transgenic plants which will express the heterologous genes in greater abundance in the roots, leaves, stems or other tissue of a plant, particularly in greater abundance in the roots than in the seed.

It is one feature of the present invention that recombinant genetic engineering is utilized to provide promoters, vectors and transgenic plants that will drive the preferential expression of associated DNA in plant tissue.

It is another feature of the present invention that promoters of metallothionein-like genes are provided which promote the preferential expression of associated DNA in plant tissue.

It is another advantage of the present invention that DNA sequences, promoters and vectors are provided that will drive the expression of associated genes in greater abundance in roots, leaves or stems than in seed.

It is another advantage of the present invention that transgenic plants are obtained in which heterologous genes may be expressed preferentially in roots, leaves or stems.

According to the present invention, a DNA sequence is provided for tissue preferential transcription of DNA. The present invention relates to promoters of metallothionein-like proteins which are able to function as tissue-specific promoters which will drive the transcription of associated DNA sequences preferentially in tissue, such as roots, such that expression of the associated DNA sequences is greater in the roots than in other tissues of the plant, particularly the seed of the plant. Thus, a protein product of the associated DNA sequences may be produced in greater amounts in the roots or other preferential tissue than in the seed of the plant.

As used in the present application, the terms "root-preferential promoter," "root-preferential expression," "tissue-preferential expression" and "preferential expression" are used to indicate that a given DNA sequence will direct a higher level of transcription of associated DNA sequences, or of expression of the product of the associated gene as indicated by any conventional RNA, DNA or protein assay, or that a given DNA sequence will demonstrate some differential effect; i.e., that the transcription of the associated DNA sequences or the expression of a gene product is greater in some tissue, for example, the roots of a plant, than in some or all other tissues of the plant, for example, the seed. "Root-preferential expression" is used to indicate a higher level of transcription of associated DNA sequences or of expression of the product of an associated gene in the root than in some or all other tissue of the plant.

As used in the present application, the term "substantial sequence homology" is used to indicate that a nucleotide sequence (in the case of DNA or RNA) or an amino acid sequence (in the case of a protein or polypeptide) exhibits substantial functional or structural equivalence with another nucleotide or amino acid sequence. Any functional or structural differences between sequences having substantial sequence homology will be de minimis; that is they will not affect the ability of the sequence to function as indicated in the present application. For example, a sequence which has substantial sequence homology with a DNA sequence disclosed to be a root-preferential promoter will be able to direct the root-preferential expression of an associated DNA sequence. Sequences that have substantial sequence homology with the sequences disclosed herein are usually variants of the disclosed sequence, such as mutations, but may also be synthetic sequences. Structural differences are considered de minimis if there is a significant amount of sequence overlap or similarity between two or more different sequences or if the different sequences exhibit similar physical characteristics. Such characteristics can include, for example, immunological reactivity, enzyme activity, structural protein integrity, etc.

Two nucleotide sequences may have substantial sequence homology if the sequences have at least 70 percent, more preferably 80 percent and most preferably 90 percent sequence similarity between them. Two amino acid sequences have substantial sequence homology if they have at least 50 percent, preferably 70 percent, and most preferably 90 percent similarity between the active portions of the polypeptides.

In the case of promoter DNA sequences, "substantial sequence homology" also refers to those fragments of a promoter DNA sequence that are able to operate to promote the expression of associated DNA sequences. Such operable fragments of a promoter DNA sequence may be derived from the promoter DNA sequence, for example, by cleaving the promoter DNA sequence using restriction enzymes, synthesizing in accordance with the sequence of the promoter DNA sequence, or may be obtained through the use of PCR technology. Mullis et al., *Meth. Enzymol.*, 155:335–350 (1987); Erlich (ed.), *PCR Technology*, Stockton Press (New York 1989).

A promoter DNA sequence is said to be "operably linked" to a second DNA sequence if the two are situated such that the promoter DNA sequence influences the transcription or translation of the second DNA sequence. For example, if the second DNA sequence codes for the production of a protein, the promoter DNA sequence would be operably linked to the second DNA sequence if the promoter DNA sequence affects the expression of the protein product from the second DNA sequence. For example, in a DNA sequence comprising a promoter DNA sequence physically attached to a coding DNA sequence in the same chimeric construct, the two sequences are likely to be operably linked.

As used herein, the terms "metallothionein-like" and "MT-like" refer to DNA sequences or amino acid sequences having sufficient sequence homology to the amino acid sequence of a metallothionein protein or the DNA sequence of a gene coding for a metallothionein protein, but whose expression has not been confirmed to be inducible by metals or has not been shown to bind metal ions.

Clone A (pCIB1325) was isolated from inbred G450; clones 11, 7, Y, 39, 2 and 13 from inbred 211D. The vertical dash line indicates the position of the Pst I site.

Figure 2:
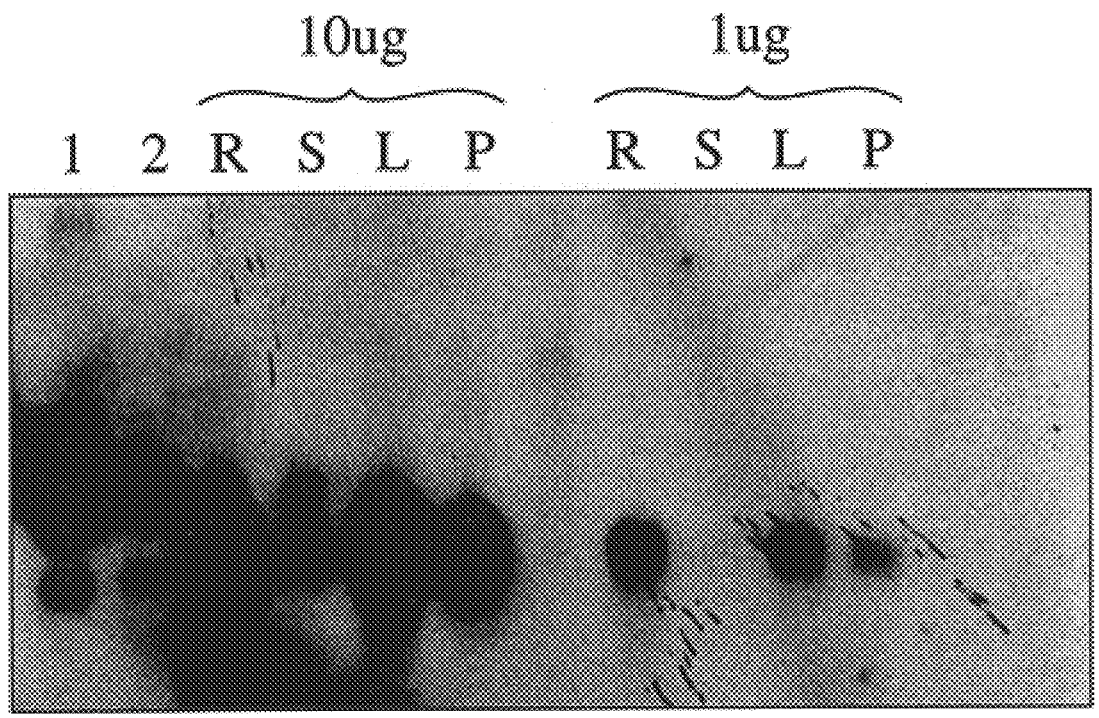

FIG. 2: Level of tissue preferential mRNA in different parts of the maize plant 10 ug and 1 ug of root (R), seed (S), leaf (L) and pith (P) total RNA were subjected to electrophoresis on a 1.2 % denaturing formaldehyde agarose gel. The RNA was blotted onto nitrocellulose and probed with nick-translated pCIB1325 cDNA insert. Lanes 1 and 2 were loaded with 200 pg and 20 pg, respectively, of cDNA insert to allow quantitation of the mRNA detected in the different tissues.

Figure 3:
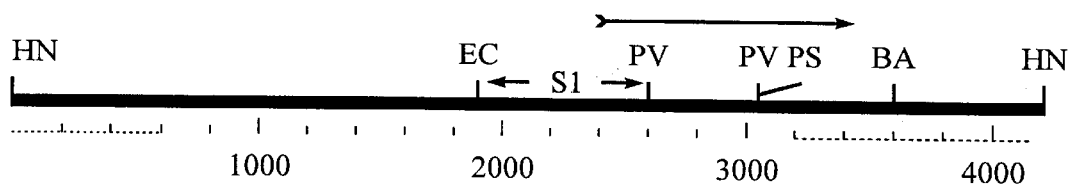

FIG. 3: Restriction map of genomic subclone pCIB1324

The arrow indicates the location of the tissue-preferential gene, as well as its 5' to 3' orientation in genomic subclone Rt-H7 (pCIB1324) . Also shown is the Eco RI-Pvu II DNA fragment (labelled S1) used for the Mung Bean nuclease mapping experiment (see FIG. 6 for details).

Figure 4:
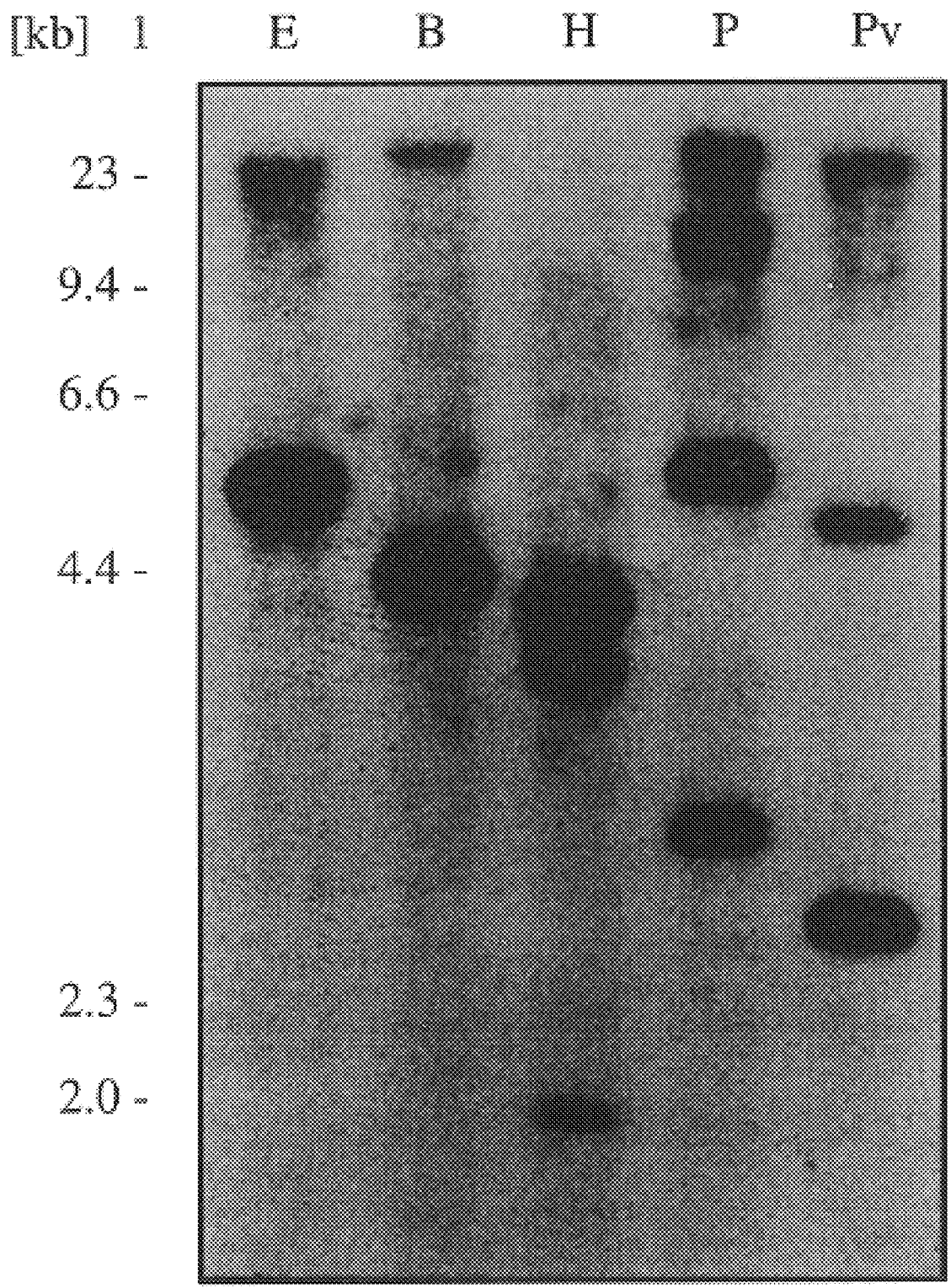

FIG. 4: Genomic Southern analysis of the tissue-preferential DNA sequence in inbred maize line 211D 5 ug of maize inbred 211D genomic DNA digested with Eco RI (E), BamHI (B), Hind III (H), Pst I (P) or Pvu II (Pv) were subjected to electrophoresis on a 0.7% agarose gel and the DNA was blotted onto nitrocellulose. pCIB1325 cDNA was nick-translated and used as a probe. Lambda DNA digested with Hind III was used as molecular weight marker in lane 1.

FIG. 5: Comparison of the tissue-preferential cDNA and genomic clone DNA sequences FIG. 5 shows the sequence of the tissue-preferential cDNA isolated from maize inbred line 211D (top sequence; SEQ ID NO. 5) and of the genomic clone (bottom sequence; SEQ ID NO:1). Only part of the intron sequence is shown in this figure. The complete intron sequence is shown in FIG. 9. The start of translation is boxed and topped with an arrow.

FIG. 6: Mung Bean nuclease mapping and primer extension Panel A: 60 ug of total root RNA were mixed with 20,000 cpm of end-labeled EcoRI-Pvu II genomic subclone (fragment S1 shown on FIG. 3). After annealing at 39° C. for 4 hours, 1 or 10 Units of Mung Bean nuclease (MB) were added and digestion was carried out at 37° C. for 1 hour. The protected DNA fragments were then extracted with phenol:chloroform, precipitated and run on a 6% sequencing gel with end-labeled molecular weight markers (pBR322 digested with Hpa II). (lane MW). The arrows indicate the positions of the protected fragments.

Panel B: 30 ug of root total RNA were annealed for 4 hours with 0.01 pmole of $32^P$-labeled primer. The primer used is underlined in the panel C sequence. Reverse-transcriptase was then added and primer extension was carried out at 37° C. for 1 hour. The extended fragments were extracted with phenol:chloroform, precipitated and run on a 6% sequencing gel (lane 5). A sequencing reaction of the genomic subclone EcoRI-PvuII primed with the kinased oligonucleotide primer used for the primer extension reaction was run on the same gel (lanes G, A, T and C) to determine precisely with which base(s) the extended fragment(s) comigrate. The arrows point to four transcription start sites.

Panel C: Sequence of the EcoRI-PvuII genomic subclone region covering the TATA box, the starts of transcription and the translational start of the tissue-preferential gene: (SEQ ID NO:2)

The sequence of the oligonucleotide used for primer extension is underlined. The arrows point to the ends of the protected fragments obtained after Mung-Bean nuclease mapping. The four transcription start sites determined by primer extension are topped with a plus (+) sign. The TATA box at position 67 and the translational start site at position 173 are boxed.

FIG. 7: Amino-acid comparison of the predicted product of the tissue-preferential gene product and a number of other metallothioneins Panel A: Alignment of the tissue-preferential gene product (SEQ ID NO:4) with that of the pea metallothionein reported by Evans et al. (SEQ ID NO:5) The vertical lines indicate matching amino acids.

Panel B: Alignment of the amino terminus domain containing the Cys-X-Cys motifs (SEQ ID NO.60 with that of other class I metallothionein proteins (SEQ ID NO: 7–9).

Panel C: Alignment of the carboxy terminus domain containing the Cys-X-Cys motifs (SEQ IDS:10) with that of other class I metallothionein proteins (SEQ ID NOS:11–13).

Figure 8:
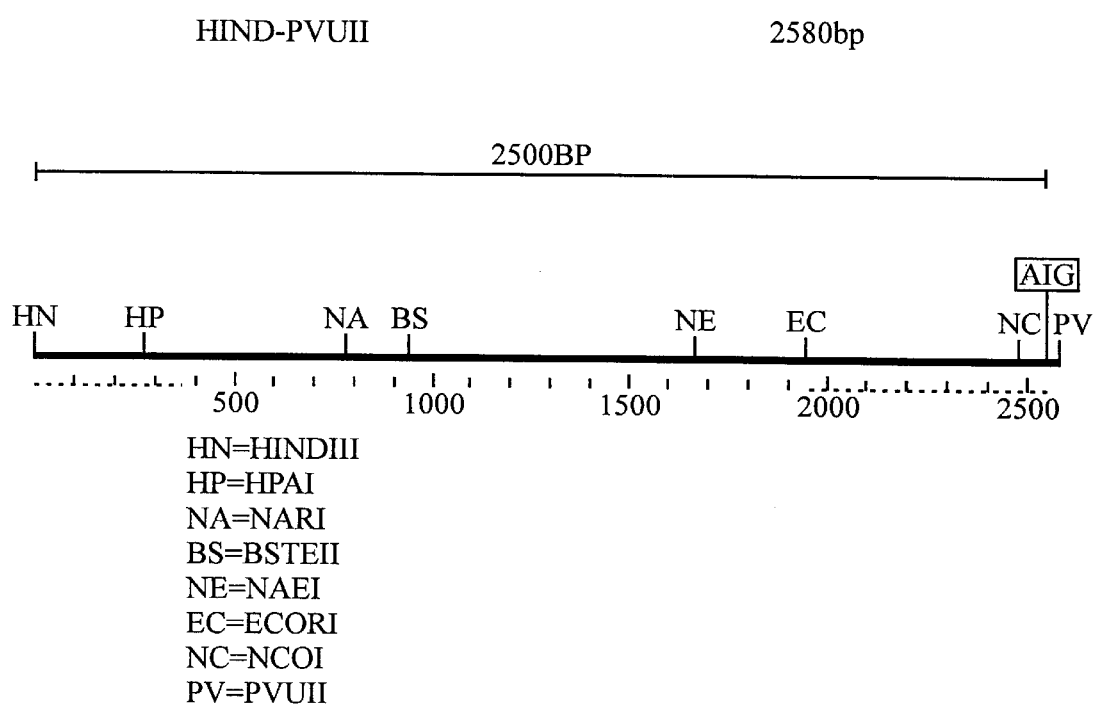

FIG. 8: Restriction map of the maize metallothionein-like gene 5' upstream region This figure shows a restriction map of the 2.5 kb fragment of the metallothionein-like gene 5' flanking sequence. This fragment was fused to the GUS bacterial reporter gene after insertion of a Bam HI site at the ATG via PCR mutagenesis. The ATG start of translation is identified by a box.

FIG. 9: Nucleotide sequence of tissue-preferential promoter

This figure shows the nucleotide sequence of the MT-like gene, including 2.5 kb of 5' flanking sequence (SEQ ID NO:1). The TATA box is found at bases 2459 to 2465 (underlined and in bold). The ATG codon representing the start of translation is found at bases 2565 to 2567. The intron extends from base 2616 through 2792. The TGA stop codon is found at bases 2969 to 2971.

Figure 10:
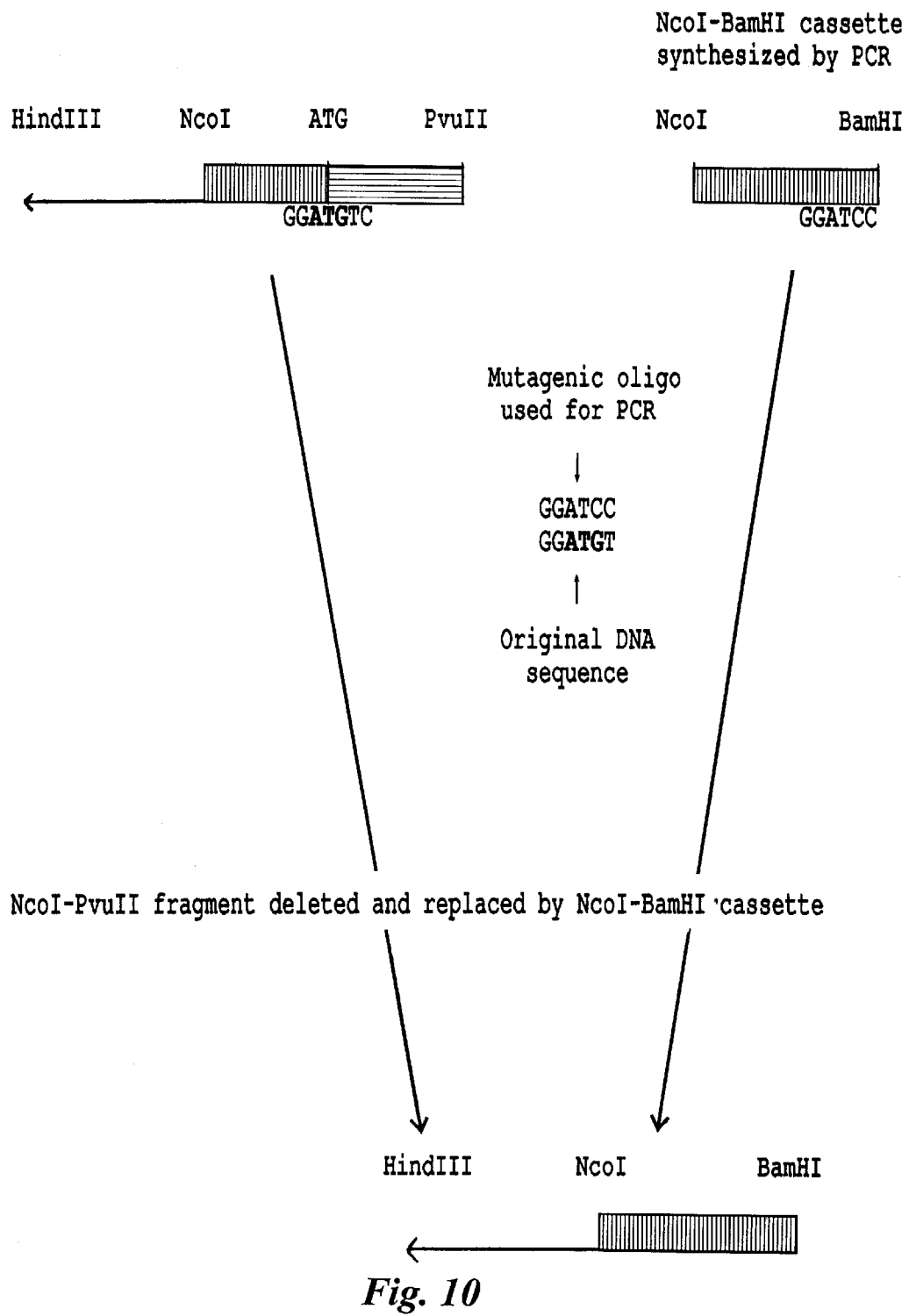

FIG. 10: Site-specific mutagenesis via PCR resulting in insertion of a BamHI site at the start of translation The drawing on the top left shows the 3' end of the Hind III-PvuII promoter fragment. Underneath it is the sequence at the ATG where a BamHI site was inserted as follows: a 96 bp NcoI-BamHI fragment (top right of figure) was synthesized using polymerase chain reaction (PCR) technology (See Mullis et al., *Meth. Enzymol.*, 155:335–350 (1987); Erlich (Ed.), *PCR Technology*, Stockton Press (New York 1989)), to copy the tissue-preferential promoter sequence from a unique NcoI site (upstream of the ATG shown in FIG. 8) to the ATG. One of the PCR primers was mutagenic in that the ATG was replaced with a BamHI site (shown in the middle of the figure). This NcoI-BamHI cassette was then cloned back into the tissue-preferential promoter clone from which the original NcoI-PvuII fragment had been deleted.

Figure 11:
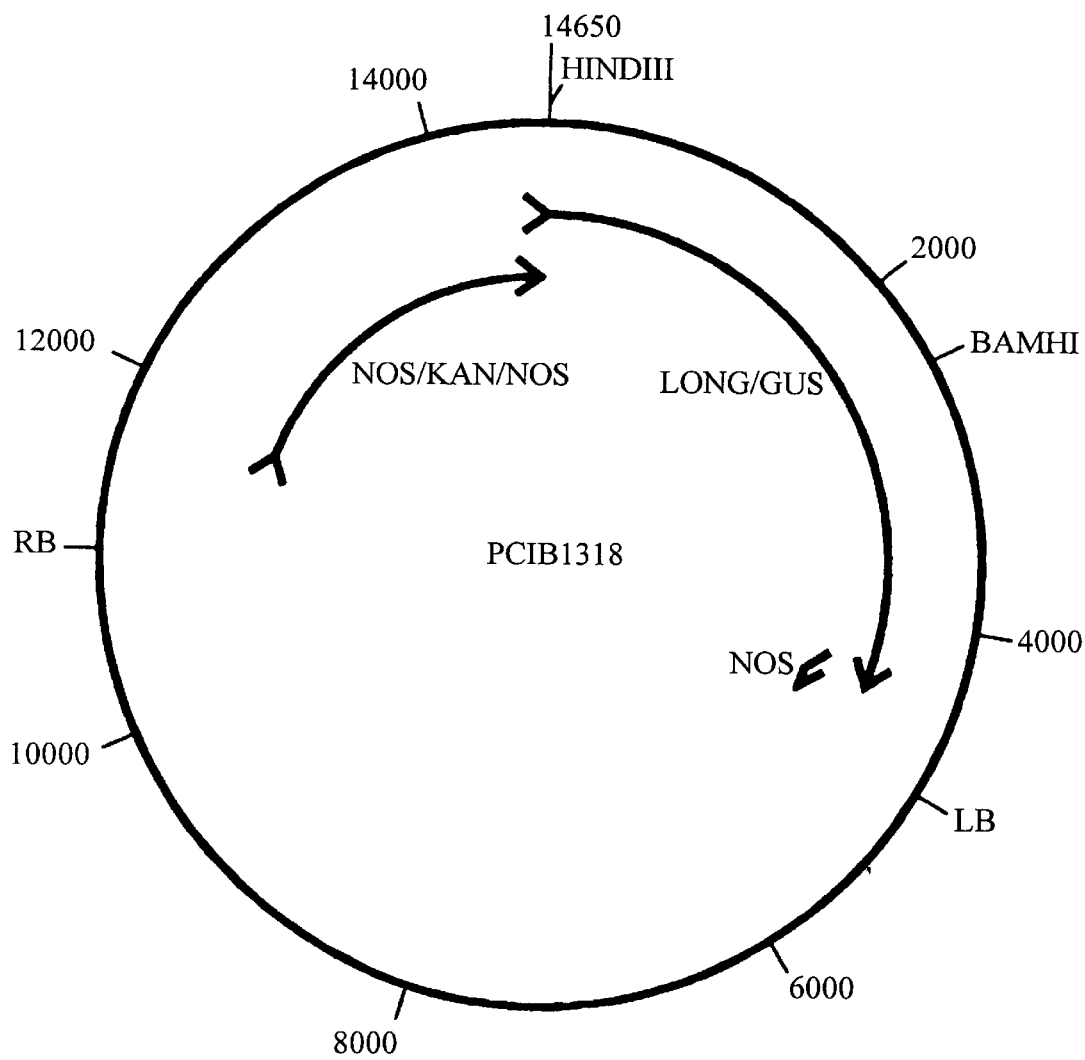

FIG. 11: Map of the binary vector pCIB1318

The Hind III-ATG fragment shown in FIG. 8, which contains 2.5 kb of 5' flanking sequence of the MT-like gene, was ligated into pBI101 (Bevans, *NAR*, 12:8711–8721 (1984)) digested with HindIII and BamHI, in front of the GUS gene. pBI101 contains kanamycin resistance genes which allow selection of both bacterial and plant cells. RB and LB stand for T-DNA right border and left border, respectively.

DETAILED DESCRIPTION OF THE INVENTION

The present invention relates to promoter DNA sequences which show tissue-preferential transcription of associated DNA sequences, such that the mRNA transcribed or protein encoded by the associated DNA sequence is produced in greater abundance in some plant tissue than in other tissue. The promoter DNA sequences of the present invention preferably direct tissue-preferential transcription in the roots, leaves and stems of a plant. The promoter DNA sequences most preferably direct tissue-preferential transcription in the roots of the plant. It is also preferred that the promoter DNA not direct tissue-preferential transcription in the seed of the plant. Thus, according to the present invention, there is provided a method of directing tissue-preferential transcription of DNA such that the DNA is transcribed in greater abundance in the roots, leaves and stems of a plant than in the seed of the plant.

Using differential hybridization, a cDNA which is very abundant in the roots of maize (inbred 211D) but is far less detectable in the kernels was cloned. Northern analysis showed that this mRNA is most abundant in roots, less abundant in green leaves and pith, with little detectable message in seed. Thus, it was determined that this mRNA is transcribed from a tissue-preferential DNA sequence. This mRNA is a little over 600 nucleotides in length. Six cDNAs were isolated from the roots of maize inbred 211D and one from maize inbred G450. Only the latter, clone A (pCIB1325), has a poly A tail, even though two of the 211D clones are longer on their 3' ends. This indicates that polyadenylation likely occurs at different sites in both inbreds. Such imprecision in choice of polyadenylation sites has been seen with other transcripts. Messing et al., *Genetic Engineering of Plants*, Plenum Press (Kossage et al. (eds.), New York 1983).

The tissue-preferential cDNA was used to screen a maize (inbred 211D) genomic library. Two genomic clones were mapped and the regions that hybridized to the cDNA were subcloned. Mapping shows that they are identical. All six cDNAs isolated from maize 211D and one genomic clone (pCIB1324) were sequenced and found to be 100% homologous (FIG. 5). Genomic Southern analysis (FIG. 4) reveals the existence of other sequences that cross-hybridize with the cDNAs isolated, although apparently not with 100% homology.

Mung Bean nuclease mapping and primer extension gave consistent results in the mapping of the transcriptional start sites of the tissue-preferential gene. There are four potential start sites (shown in FIG. 6, panel C). This allowed us to identify a putative TATA box, located at about −31 to −36, depending on the start site considered and the first ATG start of translation at position 173 (FIG. 6, panel C). Neither a poly A tail nor a polyadenylation signal is found in any of the 211D cDNAs. Even though clone A (pCIB1325) has a poly A tail, it contains no poly A signal resembling the consensus sequence (AATAAA) in the 200 base pairs preceding the tail.

Translation of the open reading frame predicts a rather small protein of about 8100 daltons in molecular weight. This leaves a 350 nt 3' untranslated region. Such long 3' untranslated regions are rare although not unprecedented in plant genes. Hawkins, *NAR*, 16:9893 (1988). The tissue-preferential gene protein is rich in the amino-acids cysteine, serine, alanine and glycine, which represent 16%, 13%, 13% and 12% of the molecule, respectively.

This 8 Kd protein encoded by the tissue-preferential gene was identified as a metallothionein-like (MT-like) protein after comparison with the pea metallothionein sequence recently described by Evans et al. FEBS 262(1):29–32 (1990). The promoter of the maize MT-like gene was mapped and sequenced up to −2500 bp upstream of the start of translation. 2.5 kb of 5' flanking sequence of the maize MT-like gene was fused to the bacterial reporter gene, b-glucuronidase (GUS), and transformed into tobacco via *Agrobacterium* binary vectors. The GUS gene driven by one such promoter construct was found to be expressed in transgenic tobacco.

As illustrated in the examples below, the DNA sequences, vectors and transgenic plants of the present invention comprise a tissue-preferential promoter isolated from a maize plant, preferably a root-preferential promoter DNA sequence. The tissue-preferential promoter DNA sequence may be isolated from a metallothionein-like gene, preferentially a maize metallothionein-like gene. The tissue-preferential promoter DNA sequence may be isolated from a plant, preferentially isolated from a maize plant, and more preferentially isolated from a maize inbred plant, such as Funk line 211D. Maize inbred lines which may be useful in the present invention include but are not limited to the following lines and their derivatives: Funk 211D, Funk 5N984, Funk 5N986, Funk 2717, Funk 0274, Funk 2N217A, B73, A632, CM105, B37, B84, B14, Mol7, R168, MS71, A188, FA91, A641 and W117.

The tissue-preferential promoter DNA sequences are preferably linked operably to a coding DNA sequence, for example a DNA sequence which is transcribed into RNA, or which is ultimately expressed in the production of a protein product. However, the tissue-preferential promoter DNA sequences are useful by themselves, for example, for use in anti-sense applications.

The tissue-preferential promoter DNA sequences of the present invention preferably comprise all or a functional fragment of the DNA sequence of FIG. 9 (SEQ ID NO: 1). The present invention also includes functional fragments of tissue-preferential promoter DNA sequences that are able to direct the tissue-preferential transcription of associated DNA sequences. The present invention also includes DNA sequences having substantial sequence homology with the tissue- preferential sequences, such that they are able to direct the tissue-preferential transcription of associated DNA sequences.

The DNA sequence associated with the regulatory or promoter DNA sequence may be heterologous or homologous. In either case, transcription of the associated DNA sequence will be directed so that the mRNA transcribed or the protein encoded by the associated DNA sequence is expressed in greater abundance in some plant tissue, such as the root, leaves or stem, than in the seed. Thus, the associated DNA sequence preferably may code for a protein that is desired to be expressed in a plant only in some tissue, such as the roots, leaves or stems, and not in the seed. Such proteins include, for example, insect selective toxins such as polypeptides from *Bacillus thuringiensis*, which are postulated to generate small pores in the insect gut cell membrane, Knowles et al., *Biochim. Biophys. Acta* 924:509–518 (1987). The associated DNA sequence may code for other proteins known to inhibit insects or plant pathogens such as fungi, bacteria and nematodes. These proteins include, for example, magainins, Zasloff, *PNAS USA* 84:5449–5453 (1987); cecropins, Hultmark et al., *EUR. J. Biochem.* 127:207–217 (1982); attacins, Hultmark et al., *EMBO J.* 2:571–576 (1983); melittin, gramicidin S, Katsu et al., *Biochim. Biophys. Acta* 939:57–63 (1988); sodium channel proteins and synthetic fragments, Oiki et al. *PNAS USA* 85:2393–2397 (1988); the alpha toxin of *Staphylococcus aureus*, Tobkes et al. *Biochem.* 24:1915–1920 (1985); apo-lipoproteins and fragments thereof, Knott et al., *Science* 230:37 (1985); Nakagawa et al., *J. Am. Chem. Soc.* 107:7087 (1985); alamethicin and a variety of synthetic amphipathic peptides, Kaiser et al., *Ann. Rev. Biophys. Biophys. Chem.* 16:561–581 (1987); and lectins, Lis et al., *Ann. Rev. Biochem.* 55: 35–68 (1986).

The recombinant DNA vectors of the present invention are those vectors that contain sequences of DNA that are required for the transcription of cloned copies of genes and for the translation of their mRNAs in a host, such as *E. coli*. Suitable expression vectors include lambda gt11, pUC8, pUC9, pWR590, pWR590-1, and pWR590-2. Preferred vectors are three expression vectors pWR590, pWR590-1 and pWR590-2, which are described in Guo et al., *Gene* 29:251–254 (1984). In these vectors, foreign DNA can be inserted into a polylinker region such that these exogenous sequences can be translated by *E. coli* cells into a fusion protein, the first 590 amino acids of which are supplied by a truncated *E. coli* b-galactosidase gene in all three possible translational reading frames.

Suitable cells for transformation of the expression plasmid include any strains that allow its replication and translation. Examples include *E. coli* strains HB101, JM101 and SF8.

The present invention also includes transgenic plants which preferably comprise a tissue-preferential promoter DNA sequence isolated from a maize plant, preferably a maize inbred plant, such as Funk line 211D. The transgenic plant is preferably a tobacco or a maize plant. The transgenic plant may be homologous, that is, the inserted genes may be from the same species as the targeted recipient plant, or heterologous, that is, the inserted genes may be from a plant of a different species than the recipient plant.

All plants from which protoplasts can be isolated and cultured to give whole regenerated plants can be transformed by the present invention so that whole plants are recovered which contain the DNA coding sequence. Some suitable plants include, for example, species from the genera Fragaria, Lotus, Medicago, Onobrychis, Trifolium, Trigonella, Vigna, Citrus, Linum, Geranium, Manicot, Daucus, Arabidopsis, Brassica, Raphanus, Sinapis, Atropa, Capsicum, Datura, Hyoscyamus, Lycopersicum, Nicotiana, Solanum, Petunia, Dactylis, Majorana, Cichorium, Helianthus, Lactuca, Bromus, Asparagus, Antirrhinum, Gossypium, Hemerocallis, Nemesia, Pelargonium, Panicum, Pennisetum, Ranunculu, Senecio, Salpiglossis, Cucumis, Browallia, Glycine, Lolium, Zea, Triticum, Sorghum and Datura.

There is an increasing body of evidence that practically all plants can be regenerated from cultured cells or tissues, including but not limited to, all major cereal crop species, sugarcane, sugar beet, cotton, fruit and other trees, legumes and vegetables.

The transgenic plants of the present invention may be transformed by any method of transformation known in the art. These methods include transformation by direct infection or co-cultivation of plants, plant tissue or cells with *Agrobacterium tumefaciens*; Horsch et al., *Science,* 225: 1229 (1985); Marton, *Cell Culture and Somatic Cell Genetic of Plants,* 1:514–521 (1984); direct gene transfer into protoplasts; Paszkowski et al., *EMBO J.* 12:2717 (1984); Loerz et al., *Mol. Gen. & Genet.* 1199:178 (1985); Fromm et al., *Nature* 319:719 (1986); microprojectile bombardment, Klein et al., *Bio/Technology,* 6:559–563 (1988); injection into protoplasts cultured cells and tissues, Reich et al., *Bio/Technology,* 4:1001–1004 (1986); or injection into meristematic tissues of seedlings and plants as described by De La Pena et al., *Nature,* 325:274–276 (1987); Graves et al., *Plant Mol. Biol.,* 7:43–50 (1986); Hooykaas-Van Slogteren et al., *Nature,* 311:763–764 (1984); Grimsley et al., *Bio/Technology,* 6:185 (1988); and Grimsley et al., *Nature,* 325:177 (1988).

The DNA sequences, vectors and plants of the present invention are useful for directing tissue-preferential mRNA and protein expression such that the mRNA is transcribed or the protein is expressed in greater abundance in some plant tissue, such as plant roots, leaves or stem, than in the seed. This is very important in controlling and directing the plant's ability to tolerate and withstand pathogens and herbivores that attack the roots, leaves or stem, for example, by locally synthesizing antipathogenic substances, while leaving the seed unaffected.

The invention is illustrated in more detail by the following examples, without implying any restriction to what is described therein.

EXAMPLES

Example 1

Plant Material and Growth Conditions

Maize plants (Zea mays Funk inbred 211D) were grown from seed in a vermiculite/sand mixture in a greenhouse under a 16-hour light/8-hour dark light regime.

Example 2

Total RNA and mRNA Isolation

Total RNA was isolated from roots, seed, leaves and pith of 2 to 5 month old green house grown plants as described in Lahners et al., *Plant Physiol.,* 88: 741–746 (1988). Poly A+RNA was purified from total RNA as described by Maniatis et al., *Molecular Cloning: A Laboratory Manual,* Cold Spring Harbor Laboratory Press:New York, (1982).

Example 3

Construction of Maize Root cDNA Libraries

Double-stranded cDNA was synthesized from maize (Funk lines G450 and 211D) root poly A+ RNA according to the procedure of Okayama et al. *Mol. Cell Biol.* 2:161 (1982). Two different libraries were made: 1) Eco RI linkers (New England Biolabs) were added, and the cDNA was cloned into lambda gt11; 2) after tailing the double-stranded cDNA with oligo-dG using polynucleotidyl-transferase, the tailed double-stranded cDNA was cloned into PstI cut oligo-dC tailed pUC9 (Pharmacia), annealed, and transformed into *E.coli* DH5a.

Example 4

Isolation of a cDNA Abundant in Maize Roots and Rare in Seeds

An amplified cDNA bank made from maize inbred line G450 root poly A+ RNA cloned in phage vector lambda gt11 was replica plated onto nitrocellulose filters. These filters were differentially screened to identify plaques hybridizing to radioactively labeled first strand cDNA from root poly A+ RNA, but not to first strand cDNA from seed poly A+ RNA. Six plaques (out of 5000 screened) were purified and the cDNA inserts were subcloned into pUC19. Northern blots carrying total RNA from root and seed were probed with these clones to confirm their tissue-specificity.

Only two clones showed high expression in root and very little detectable expression in seed. They turned out to cross-hybridize, but sequencing revealed that they were both chimeric cDNAs: several cDNAs ligated together into the same vector phage. Northern analysis was used to identify a small subclone of these chimeric cDNAs that exhibited the desired tissue preference (root versus seed). This small subclone was then used as a probe to screen other cDNA banks (from Funk lines G450 and 211D) in pUC19. Seven cDNA clones, one from G450 (clone A, pCIB1325) and six from 211D (clones Y, 2, 7 (pCIB1324), 11, 13 and 39) were purified and sequenced (see FIG. 1).

The cDNA clones from 211D were of various lengths, ranging in size from approximately 244 bp to approximately 500 bp. pCIB1325 from G450 was the longest, approximately 600 bp long. Northern analysis (FIG. 2) shows the differential expression of this mRNA in various parts of the maize plant. The mRNA is short, between approximately 600 nucleotides, the length of cDNA pCIB1325, and about 800 nucleotides (this mRNA was found to be smaller than the mRNA for the small subunit of Rubisco mRNA—data not shown). This mRNA is quite abundant in root, less abundant in leaf and pith and a lot less abundant in seed.

Example 5

DNA Isolation and Construction of Genomic Library

Plasmid DNA was purified using standard procedures and recombinant lambda DNA was extracted from plate lysates as described in Maniatis (1982). Plant DNA was isolated from leaves using the method of Shure et al., *Cell* 35:225–233 (1983). This DNA was sent to Stratagene for construction of a genomic library.

Sau3A partial digests of 211D genomic DNA were cloned into the Bam HI site of Stratagene's Lambda Dash vector. Screening of the amplified library with pCIB1325 as a probe yielded numerous plaques, some hybridizing very strongly to the probe, others more weakly. Two of the strongly hybridizing clones were purified and mapped. Both carried a 4.2 kb Hind III fragment which hybridized to pCIB1325. Subcloning and mapping of both Hind III fragments showed that they were identical. FIG. 3 shows the map of this subclone labeled Rt-H7 (pCIB1324). Fragments from pCIB1324 were then subcloned for sequencing.

Example 6

Mapping of Genomic Clones

Recombinant genomic clones were mapped directly in lambda by measuring the sizes of partial restriction enzyme digests after hybridization to a vector probe (Kohara et al., *Cell,* 50: 495–508 (1987)).

Example 7

Southern and Northern Blots Hybridizations

Southern and Northern blots were done with nitrocellulose filters as described in Maniatis (1982). Prehybridizations were in 6X SSC, 50 mM NaPO4, 5X Denhardts, 0.1 mg/ml sheared denatured calf-thymus DNA and 0.1% SDS at 68° C. for 6 to 12 hours; hybridizations were done overnight at 68° C. in the same buffer to which $1\times10^6$ cpm/ml nick-translated DNA probe (about $1\times10^8$ cpm/ug) was added. Washes were as described in Maniatis (1982). Genomic Southern blots were hybridized and washed according to Klessig et al., *Plant Molec. Biol. Rptr.,* 1:12–18 (1983).

Example 8

Gene Copy Number

In order to determine how many genes in the maize genome hybridize with the isolated maize MT-like gene, 211D genomic DNA was digested with Eco RI, Bam HI, Hind III, Pst I and Pvu II. Southern blot analysis of these DNAs using pCIB1325 as a probe is shown in FIG. 4. As can be seen, each digest shows one very intense band, and in some cases (Hind III, PvuII and Pst I) 1 or 2 additional, fainter bands. The most intense bands can be assigned to the isolated genomic clone. The fainter bands can be explained by assuming that there is another gene in the maize genome, which cross-hybridizes with the tissue-preferential gene, but is not 100% homologous to it. This is consistent with the isolation of two classes of plaques during the screening of the genomic library, some plaques hybridizing very intensely to the cDNA probe, others more weakly.

Example 9

Sequencing of the Maize MT-like cDNAs and Genomic Clones

DNA was sequenced using the dideoxy chain-termination method of Sanger et al. *PNAS USA* 74:5463–5467 (1977), using double-stranded plasmid DNA as a template. For part of the sequence, the chemical DNA sequencing technique of Maxam and Gilbert *PNAS USA* 74:560–564 (1977) was used. All DNA sequence analysis was carried out on a Digital Vax 8530 computer using the University of Wisconsin Computer Genetics Group software. The oligonucleotide primers were synthesized on an Applied Biosystems Model 380A Synthesizer.

Figure 1:
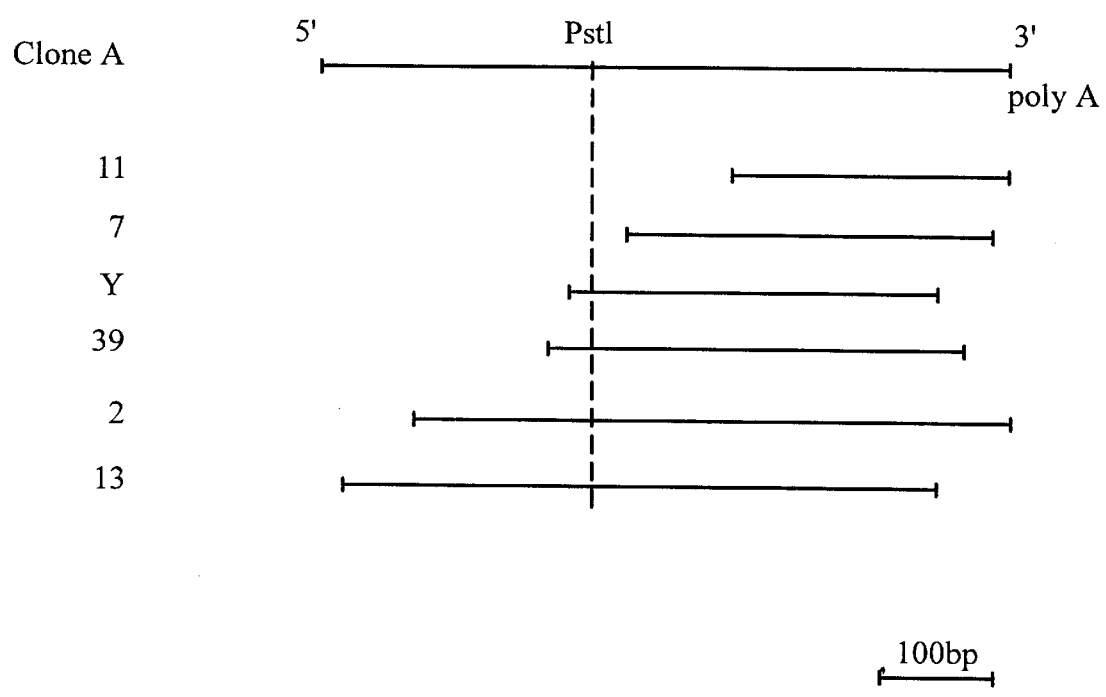
FIG. 1: Restriction maps of the tissue preferential cDNAs

Sequencing of the six cDNAs isolated from 211D described in FIG. 1 were all identical in the overlapping regions (data not shown). FIG. 5 shows that the sequence of genomic clone pCIB1324 is identical to that of the cDNAs, except for a single 175 bp intron. Only pCIB1325, isolated from inbred G450, has a poly A tail. The other six clones, from inbred 211D, are truncated on their 3' end and do not have a poly A tail. cDNAs 2 and 11 are 19 and 17 nucleotides longer, respectively, than pCIB1325 on their 3' end. Therefore, the exact length of the 211D mRNA could not be determined. Differential polyadenylation sites may be involved. Messing et al., *Genetic Engineering of Plants, pp.* 211–227 (Kosuge et al., eds., Plenum Press, New York 1983).

Example 10

Mung Bean Nuclease Mapping and Primer Extension

The start of transcription of the tissue-preferential gene was mapped by the single-stranded nuclease method developed by Berk et al. *Cell*, 12: 721 (1977) and primer extension.

60 ug of root total RNA was mixed with 20,000 cpm of an end-labeled DNA restriction fragment, precipitated with ethanol and resuspended in 25 ul of hybridization buffer (40 mM PIPES pH6.4, 1 mM EDTA, 0.4 M NaCl, 80% formamide). The mixtures were heated at 72° C. for 15 minutes, then transferred to a 39° C. water bath for 4 hours. After annealing, 500 ul of ice cold Mung Bean nuclease buffer (30mM NaOAc pH4.6, 50 mM NaCl, 1 mM $ZnCl_2$, 5% glycerol and 1 or 10 units of Mung Bean nuclease (Pharmacia) was added and incubated at 37° C. for 60 min. The reaction was stopped by the addition of 50 ul of 5 M NH4OAc, 80 mM EDTA, 200 ug/ml tRNA and extracted once with phenol:chloroform. The DNA/RNA hybrid was precipitated with isopropanol, rinsed with ethanol and resuspended in sequencing loading dye. The sizes of the protected fragments were determined by electrophoresis on 6% acrylamide-urea sequencing gels.

Example 11

Primer Extension

The primer was end-labeled using $^{32}P$-γATP (6000 Ci/mMole) (Amersham) and polynucleotide kinase. Metraux et al., *PNAS USA* 86:846–900 (1989). 30 ug of root total RNA were mixed with 0.01 pmole of primer in 20 ul of reverse transcriptase buffer (50 mM Tris pH7.5, 40 mM KCl, 3 mM $MgCl_2$) The mixture was heated at 80 ° C. for 10 min, then slowly cooled to 40° C. for annealing, and hybridized for 4 hrs at 40° C. To each 20 ul reaction were added 30 ul of 6 mM DTT, 0.1 mg/ml BSA, 1 mM each of dATP, dCTP, dGTP and dTTP in reverse transcriptase buffer containing 100 Units of RNAsin (Promega) and 5 Units of AMV reverse transcriptase (BRL). Primer extension was carried out at 40° C. for 60 min. The DNA/RNA hybrid was extracted once with phenol:chloroform and ethanol pricipitated in the presence of carrier DNA. The pellet was dissolved in sequencing loading mix (deionized formamide containing 0.3% xylene cyanol, 0.3% bromophenol blue and 0.37% EDTA) and analyzed on a sequencing gel as above.

Example 12

Mapping the Start of Transcription of the MT-Like Gene

Using Mung Bean nuclease mapping and primer extension, the start of transcription of the MT-like gene has been accurately mapped (FIG. 6). For the Mung-bean mapping (Panel A), annealing was at 39° C. The arrows indicate at least three protected fragments, ranging in size from 85 to 95 bp in length. This would place the start of the mRNA between bp 85 and 98 of the Eco RI-Pvu II sequence shown by the two arrows on panel C. In panel B, primer extension products run with the sequence of the genomic clone revealed four clustered start sites, topped with plus signs (+) in the sequence of panel C (SEQ ID NO:2) at positions 98, 99, 102 and 103.

Example 13

Translation of the MT-Like mRNA

The 5' untranslated leader is 70 to 75 nucleotides long. The first ATG is found at position 173 of the sequence in FIG. 6 (SEQ ID NO:2) and there is a TATA box at position 67, that is at −31 to −36 upstream of the different transcriptional start sites. The predicted protein encoded by the open reading frame is 76 amino acids in length (~8100 Kd), and terminates with a UGA stop codon at the 77th position. The amino acid sequence of this predicted protein is shown in FIG. 7, Panel A (SEQ ID NO:4).

Example 14

Identification of the protein encoded by the tissue preferential gene

The 8 Kd protein encoded by the maize MT-like gene (SEQ ID NO:4) was shown to have substantial homology to metallothionein proteins after comparison of its sequence with that of the pea metallothionein-like sequence recently described by Evans et al. FEBS 262(1):29–32 (1990) (SEQ ID NO:5) (See FIG. 7). It has not yet been demonstrated whether the maize MT-like gene is induced by metals.

Example 15

Mapping of the tissue-preferential gene promoter

The 5' flanking region of the maize MT-like gene was mapped up to 2.5 kb upstream of the ATG and sequenced (See the map of the 2.5 kb HindIII-PvuII promoter fragment and its sequence in FIGS. 8 and 9, respectively).

Example 16

Fusions of MT-like gene promoter sequence to the GUS gene to create a vector for stable plant transformation The 2.5 kb 5'-flanking regions of the MT-like gene was fused to the bacterial reporter gene for glucuronidase (GUS) in order to characterize the promoter of the MT-like gene in transgenic plants. The 2.5 kb HindIII-ATG promoter fragment shown in FIG. 8 was fused to the GUS gene after insertion of a BamHI site at the ATG as described in FIG. 10.

The resulting HindIII-BamHI promoter fragment was then fused to the GUS gene in pBI101, a binary vector system (Bevans) for stable plant transformation via *Agrobacterium tumefaciens*, resulting in plasmid pCIB1318 (FIG. 11).

Example 17

Stable transformation of pCIB1318 into tobacco using *Agrobacterium* vectors Agrobacterium strain containing the helper plasmid pCIB542 and plasmid pCIBl318 was used to transform tobacco leaf disks of four week old shoot tip cultures as described by Horsch et al. *Science*, 227: 1229–1231 (1985) except that nurse cultures were omitted and selection was performed on kanamycin at 100 mg/liter. Transgenic tobacco plants were regenerated and the presence of transforming DNA was confirmed using PCR. Various parts of these plants were then assayed for GUS activity in order to determine the pattern of expression of the GUS gene driven by the MT-like promoter sequence (in pCIB1318 transgenic plants).

Example 18

Histochemical Gus assays

Tissue transformed with pCIB1318 was incubated in assay mix (Jefferson, *Plant Mol. Biol. Rptr.*, 5: ) at 26° C. in the dark for 72 hours, then observed under a dissecting microscope for presence of blue color indicating GUS enzyme activity.

Table 1 shows the results of these histochemical assays. pCIB1318 has been deposited with ATCC and has been designated ATCC Accession Number 40762.

TABLE 1

| | Number of Plants that test GUS positive (18 Plants Total) | | |
|---|---|---|---|
| Date Assayed | 12/89 -1/90 | 2/90 | 3/90 |
| Root | 7 | 1 | 0 |
| Stem | 4 | 4 | 2 |
| Leaf | 2 | 0 | 0 |

The expression pattern of the GUS gene driven by the MT-like promoter fragment shows some variability, depending upon the transgenic plant examined. This may be explained by the so-called position effect. The position effect hypothesizes that a promoter-gene complex will be expressed differently depending upon the location this complex is integrated into a cell's genome. Another possible explanation is that gene rearrangements or deletions may have occurred. Finally, the age of the plant and their culture conditions may influence the level of expression of the chimeric gene.

While the present invention has been described with reference to specific embodiments thereof, it will be appreciated that numerous variations, modifications, and embodiments are possible, and accordingly, all such variations, modifications and embodiments are to be regarded as being within the spirit and scope of the present invention.

What is claimed is:

1. A transgenic plant comprising a chimeric gene, wherein said chimeric gene comprises a promoter sequence comprised within the region of SEQ ID NO: 1 between nucleotides 1 and 2564 operably linked to a coding sequence of interest, wherein said promoter sequence directs transcription of said coding sequence of interest.

2. A transgenic plant of claim 1, wherein the plant is a tobacco plant.

3. A transgenic plant of claim 1, wherein the plant is a maize plant.

4. A transgenic plant of claim 1, wherein said coding sequence of interest encodes a *Bacillus thuringiensis* insect toxin.

5. A transgenic plant comprising a chimeric gene wherein said chimeric gene comprises:
   a) the promoter sequence located at nucleotide positions 1 to 2564 of the gene set forth in SEQ ID NO:1;
   b) a coding sequence of interest; and
   c) a 3' terminal sequence;
   wherein said promoter sequence directs the transcription of said coding sequence.

6. A transgenic plant of claim 5, wherein said coding sequence of interest encodes a *Bacillus thurinigiensis* insect toxin.

7. A transgenic plant comprising recombinant DNA vector pCIB 1318.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 3509 base pairs
        (B) TYPE: nucleic acid (C) STRANDEDNESS: single
        (D) TOPOLOGY: linear (ii) MOLECULE TYPE: DNA (genomic)

(ix) FEATURE:
        (A) NAME/KEY: intron
        (B) LOCATION: 2617..2792

(ix) FEATURE:
        (A) NAME/KEY: TATA_signal
        (B) LOCATION: 2459..2465

(ix) FEATURE:
        (A) NAME/KEY: promoter
        (B) LOCATION: 1..2564
        (C) IDENTIFICATION METHOD: experimental
        (D) OTHER INFORMATION: /function= "Promotes
            root-preferential transcription"
            /evidence= EXPERIMENTAL (ix) FEATURE:
        (A) NAME/KEY: terminator
        (B) LOCATION: 2969..2971
        (D) OTHER INFORMATION: /standard_name= "Stop codon"

(xi) SEQUENCE DESCRIPTION: SEQ ID NO:1:

```
AAGCTTGCAC ATGACAACAA TTGTAAGAGG ATGGAGACCA CAACGATCCA ACAATACTTC      60

TGCGACGGGC TGTGAAGTAT AGAGAAGTTA AACGCCCAAA AGCCATTGTG TTTGGAATTT     120

TTAGTTATTC TATTTTTCAT GATGTATCTT CCTCTAACAT GCCTTAATTT GCAAATTTGG     180

TATAACTACT GATTGAAAAT ATATGTATGT AAAAAAATAC TAAGCATATT TGTGAAGCTA     240

AACATGATGT TATTTAAGAA AATATGTTGT TAACAGAATA AGATTAATAT CGAAATGGAA     300

ACATCTGTAA ATTAGAATCA TCTTACAAGC TAAGAGATGT TCACGCTTTG AGAAACTTCT     360

TCAGATCATG ACCGTAGAAG TAGCTCTCCA AGACTCAACG AAGGCTGCTG CAATTCCACA     420

AATGCATGAC ATGCATCCTT GTAACCGTCG TCGCCGCTAT AAACACGGAT AACTCAATTC     480

CCTGCTCCAT CAATTTAGAA ATGAGCAAGC AAGCACCCGA TCGCTCACCC CATATGCACC     540

AATCTGACTC CCAAGTCTCT GTTTCGCATT AGTACCGCCA GCACTCCACC TATAGCTACC     600

AATTGAGACC TTTCCAGCCT AAGCAGATCG ATTGATCGTT AGAGTCAAAG AGTTGGTGGT     660

ACGGGTACTT TAACTACCAT GGAATGATGG GGCGTGATGT AGAGCGGAAA GCGCCTCCCT     720

ACGCGGAACA ACACCCTCGC CATGCCGCTC GACTACAGCC TCCTCCTCGT CGGCCGCCCA     780

CAACGAGGGA GCCCGTGGTC GCAGCCACCG ACCAGCATGT CTCTGTGTCC TCGTCCGACC     840

TCGACATGTC ATGGCAAACA GTCGGACGCC AGCACCAGAC TGACGACATG AGTCTCTGAA     900

GAGCCCGCCA CCTAGAAAGA TCCGAGCCCT GCTGCTGGTA GTGGTAACCA TTTTCGTCGC     960

GCTGACGCGG AGAGCGAGAG GCCAGAAATT TATAGCGACT GACGCTGTGG CAGGCACGCT    1020

ATCGGAGGTT ACGACGTGGC GGGTCACTCG ACGCGGAGTT CACAGGTCCT ATCCTTGCAT    1080

CGCTCGGGCC GGAGTTTACG GGACTTATCC TTACGACGTG CTCTAAGGTT GCGATAACGG    1140

GCGGAGGAAG GCGTGTGGCG TGCGGAGACG GTTTATACAC GTAGTGTGCG GGAGTGTGTT    1200

TCGTAGACGC GGGAAAGCAC GACGACTTAC GAAGGTTAGT GGAGGAGGAG GACACACTAA    1260

AATCAGGACG CAAGAAACTC TTCTATTATA GTAGTAGAGA AGAGATTATA GGAGTGTGGG    1320

TTGATTCTAA AGAAAATCGA CGCAGGACAA CCGTCAAAAC GGGTGCTTTA ATATAGTAGA    1380

TATATATATA TAGAGAGAGA GAGAAAGTAC AAAGGATGCA TTTGTGTCTG CATATGATCG    1440

GAGTATTACT AACGGCCGTC GTAAGAAGGT CCATCATGCG TGGAGCGAGC CCATTTGGTT    1500

GGTTGTCAGG CCGCAGTTAA GGCCTCCATA TATGATTGTC GTCGGGCCCA TAACAGCATC    1560
```

-continued

```
TCCTCCACCA GTTTATTGTA AGAATAAATT AAGTAGAGAT ATTTGTCGTC GGGCAGAAGA      1620

AACTTGGACA AGAAGAAGAA GCAAGCTAGG CCAATTTCTT GCCGGCAAGA GGAAGATAGT      1680

GGCCTCTAGT TTATATATCG GCGTGATGAT GATGCTCCTA GCTAGAAATG AGAGAAGAAA      1740

AACGGACGCG TGTTTGGTGT GTGTCAATGG CGTCCATCCT TCCATCAGAT CAGAACGATG      1800

AAAAAGTCAA GCACGGCATG CATAGTATAT GTATAGCTTG TTTTAGTGTG GCTTTGCTGA      1860

GACGAATGAA AGCAACGGCG GGCATATTTT TCAGTGGCTG TAGCTTTCAG GCTGAAAGAG      1920

ACGTGGCATG CAATAATTCA GGGAATTCGT CAGCCAATTG AGGTAGCTAG TCAACTTGTA      1980

CATTGGTGCG AGCAATTTTC CGCACTCAGG AGGGCTAGTT TGAGAGTCCA AAAACTATAG      2040

GAGATTAAAG AGGCTAAAAT CCTCTCCTTA TTTAATTTTA AATAAGTAGT GTATTTGTAT      2100

TTTAACTCCT CCAACCCTTC CGATTTTATG GCTCTCAAAC TAGCATTCAG TCTAATGCAT      2160

GCATGCTTGG CTAGAGGTCG TATGGGGTTG TTAATAGCAT AGCTAGCTAC AAGTTAACCG      2220

GGTCTTTTAT ATTTAATAAG GACAGGCAAA GTATTACTTA CAAATAAAGA ATAAAGCTAG      2280

GACGAACTCG TGGATTATTA CTAAATCGAA ATGGACGTAA TATTCCAGGC AAGAATAATT      2340

GTTCGATCAG GAGACAAGTG GGGCATTGGA CCGGTTCTTG CAAGCAAGAG CCTATGGCGT      2400

GGTGACACGG CGCGTTGCCC ATACATCATG CCTCCATCGA TGATCCATCC TCACTTGCTA      2460

TAAAAAGAGG TGTCCATGGT GCTCAAGCTC AGCCAAGCAA ATAAGACGAC TTGTTTCATT      2520

GATTCTTCAA GAGATCGAGC TTCTTTTGCA CCACAAGGTC GAGGATGTCT TGCAGCTGCG      2580

GATCAAGCTG CGGCTGCGGC TCAAGCTGCA AGTGCGGGTA ATATATAATA ATATATAAGT      2640

GCACCGTGCA TGATTAATTT CTCCAGCCTT CTTCTTGTCT TGTCTAGTTA ATTTCCCTTC      2700

TTTATTTATT TTTTCCATTG CAAAACAAAC AAACAAAAAA CAAAGTTAAT CTGGATCGAG      2760

TAGTTCAATC CATTTGCGCG CTGTCCTTTT CAGCAAGAAG TACCCTGACC TGGAGGAGAC      2820

GAGCACCGCC GCGCAGCCCA CCGTCGTCCT CGGGGTGGCC CCGGAGAAGA AGGCCGCGCC      2880

CGAGTTCGTC GAGGCCGCGG CGGAGTCCGG CGAGGCCGCC CACGGCTGCA GCTGCGGTAG      2940

CGGCTGCAAG TGCGACCCCT GCAACTGCTG ATCACATCGA TCGACGACCA TGGATATGAT      3000

TATTATCTAT CTAGCTTGTG GTGGTGGTTG AACAATAATA AGCGAGGCCG AGCTGGCTGC      3060

CATACATAGG TATTGTGTGG TGTGTGTGTG AGAGAGAGAG AAACAGAGTT CTTCAGTTTG      3120

CTATCTCTCT CTGCATGTTT GGCGTCAGTC TTTGTGCTCA TGTACGTGTG TCTACATGCA      3180

TGTTGGTTGA TCCGATTGCG TCTGCTGTAA CCATATATTA ATTGGTCCAC GATGATATGA      3240

TTTGATACTA TATATATATA CTAAAACCGG ACTTATTATA ATACTTGTAG TATATAAGTT      3300

TCTTACGCCG CAATTGATCG ATTCAGAACG AAGGAGTTCT AGCTAGCTAA AACATGCAGA      3360

TTCAGAATAT CAGATTTTAC GACTACTGGA GGACAAGAAT ATTTCACTGT CACCAAACTA      3420

AAATCCACTT GTTCAAATCT TCAGACGCCG TGTATGATCG AACCACCACT TTGTACTGTA      3480

TATCCTAGTA TCTATACAAA TATGGATCC                                        3509
```

(2) INFORMATION FOR SEQ ID NO:2:

(i) SEQUENCE CHARACTERISTICS:
        (A) LENGTH: 183 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..183

(D) OTHER INFORMATION: /note= "Sequence of the EcoRI-PvuII
                   subclone containing the TATA box and translation start
                   codon. Sequence is identical to that found at nucleotide
                   positions 2393 to 2575 (inclusive) of SEQ ID NO:1"

(ix) FEATURE:
              (A) NAME/KEY: TATA_signal
              (B) LOCATION: 67..74
              (C) IDENTIFICATION METHOD: experimental
              (D) OTHER INFORMATION: /evidence= EXPERIMENTAL (ix) FEATURE:
              (A) NAME/KEY: misc_feature
              (B) LOCATION: 173..175
              (C) IDENTIFICATION METHOD: experimental
              (D) OTHER INFORMATION: /function= "Translation start
                   codon"
                   /evidence= EXPERIMENTAL (xi) SEQUENCE DESCRIPTION: SEQ ID NO:2:

TATGGCGTGG TGACACGGCG CGTTGCCCAT ACATCATGCC TCCATCGATG ATCCATCCTC     60

ACTTGCTATA AAAAGAGGTG TCCATGGTGC TCAAGCTCAG CCAAGCAAAT AAGACGACTT    120

GTTTCATTGA TTCTTCAAGA GATCGAGCTT CTTTTGCACC ACAAGGTCGA GGATGTCTTG    180

CAG                                                                 183

(2) INFORMATION FOR SEQ ID NO:3:

(i) SEQUENCE CHARACTERISTICS:
              (A) LENGTH: 580 base pairs
              (B) TYPE: nucleic acid
              (C) STRANDEDNESS: single
              (D) TOPOLOGY: linear (ii) MOLECULE TYPE: cDNA (ix) FEATURE:
              (A) NAME/KEY: misc_feature
              (B) LOCATION: 1..580
              (D) OTHER INFORMATION: /note= "cDNA sequence of the tissue
                   preferential transcript."

(xi) SEQUENCE DESCRIPTION: SEQ ID NO:3:

ATTCTTCAAG AGATCGAGCT TCTTTTGCAC CACAAGGTCG AGGATGTCTT GCAGCTGCGG     60

ATCAAGCTGC GGCTGCGGCT CAAGCTGCAA GTGCGGCAAG AAGTACCCTG ACCTGGAGGA    120

GACGAGCACC GCCGCGCAGC CCACCGTCGT CCTCGGGGTG GCCCCGGAGA AGAAGGCCGC    180

GCCCGAGTTC GTCGAGGCCG CGGCGGAGTC CGGCGAGGCC GCCCACGGCT GCAGCTGCGG    240

TAGCGGCTGC AAGTGCGACC CCTGCAACTG CTGATCACAT CGATCGACGA CCATGGATAT    300

GATTATTATC TATCTAGCTT GTGGTGGTGG TTGAACAATA ATAAGCGAGG CCGAGCTGGC    360

TGCCATACAT AGGTATTGTG TGGTGTGTGT GTGAGAGAGA GAGAAACAGA GTTCTTCAGT    420

TTGCTATCTC TCTCTGCATG TTTGGCGTCA GTCTTTGTGC TCATGTACGT GTGTCTACAT    480

GCATGTTGGT TGATCCGATT GCGTCTGCTG TAACCATATA TTAATTGGTC CACGATGATA    540

TGATTTGATA CTATATATAT ATACTAAAAC CGGACTTATT                         580

(2) INFORMATION FOR SEQ ID NO:4:

(i) SEQUENCE CHARACTERISTICS:
              (A) LENGTH: 76 amino acids
              (B) TYPE: amino acid
              (C) STRANDEDNESS: single
              (D) TOPOLOGY: linear (ii) MOLECULE TYPE: protein (ix) FEATURE:

```
          (A) NAME/KEY: Protein
          (B) LOCATION: 1..76
          (D) OTHER INFORMATION: /note= "Predicted protein product
              of tissue-preferential gene."

(xi) SEQUENCE DESCRIPTION: SEQ ID NO:4:

Met Ser Cys Ser Cys Gly Ser Ser Cys Gly Cys Ser Ser Cys Lys
1               5                   10                  15

Cys Gly Lys Lys Tyr Pro Asp Leu Glu Glu Thr Ser Thr Ala Ala Gln
            20                  25                  30

Pro Thr Val Val Leu Gly Val Ala Pro Glu Lys Lys Ala Ala Pro Glu
        35                  40                  45

Phe Val Glu Ala Ala Ala Glu Ser Gly Glu Ala Ala His Gly Cys Ser
    50                  55                  60

Cys Gly Ser Gly Cys Lys Cys Asp Pro Cys Asn Cys
65                  70                  75

(2) INFORMATION FOR SEQ ID NO:5:

(i) SEQUENCE CHARACTERISTICS:
         (A) LENGTH: 75 amino acids
         (B) TYPE: amino acid
         (C) STRANDEDNESS: single
         (D) TOPOLOGY: linear (ii) MOLECULE TYPE: protein (ix) FEATURE:
         (A) NAME/KEY: Protein
         (B) LOCATION: 1..75
         (D) OTHER INFORMATION: /note= "Protein product of pea
             metallothionein reported by Evans et al."

(xi) SEQUENCE DESCRIPTION: SEQ ID NO:5:

Met Ser Gly Cys Gly Cys Gly Ser Ser Cys Asn Cys Gly Asp Ser Cys
1               5                   10                  15

Lys Cys Asn Lys Arg Ser Ser Gly Leu Ser Tyr Ser Glu Met Glu Thr
            20                  25                  30

Thr Glu Thr Val Ile Leu Gly Val Gly Pro Ala Lys Ile Gln Phe Glu
        35                  40                  45

Gly Ala Glu Met Ser Ala Ala Ser Glu Asp Gly Gly Cys Lys Cys Gly
    50                  55                  60

Asp Asn Cys Thr Cys Asp Pro Cys Asn Cys Lys
65                  70                  75

(2) INFORMATION FOR SEQ ID NO:6:

(i) SEQUENCE CHARACTERISTICS:
         (A) LENGTH: 16 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..16
         (D) OTHER INFORMATION: /note= "amino terminal domain
             containing cys-x-cys motif of tissue-preferential gene
             product"

(xi) SEQUENCE DESCRIPTION: SEQ ID NO:6:

Ser Cys Ser Cys Gly Ser Ser Cys Gly Cys Ser Ser Cys Lys Cys
1               5                   10                  15
```

(2) INFORMATION FOR SEQ ID NO:7:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..17
        (D) OTHER INFORMATION: /note= "amino terminus domain
            containing the cys-x-cys motif of pea metallothionein"

(xi) SEQUENCE DESCRIPTION: SEQ ID NO:7:

Ser Gly Cys Gly Cys Gly Ser Ser Cys Asn Cys Gly Asp Ser Cys Lys
1               5                   10                  15

Cys (2) INFORMATION FOR SEQ ID NO:8:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..17
        (D) OTHER INFORMATION: /note= "amino terminus domain
            containing the cys-x-cys motif of equine MT-1A"

(xi) SEQUENCE DESCRIPTION: SEQ ID NO:8:

Cys Ser Cys Pro Thr Gly Gly Ser Cys Thr Cys Ala Gly Ser Cys Lys
1               5                   10                  15

Cys (2) INFORMATION FOR SEQ ID NO:9:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..17
        (D) OTHER INFORMATION: /note= "amino terminus domain
            containing the cys-x-cys motif of N. crassa
            metallothionein"

(xi) SEQUENCE DESCRIPTION: SEQ ID NO:9:

Cys Gly Cys Ser Gly Ala Ser Ser Cys Asn Cys Gly Ser Gly Cys Ser
1               5                   10                  15

Cys (2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
            (A) NAME/KEY: Peptide
            (B) LOCATION: 1..14
            (D) OTHER INFORMATION: /note= "carboxy terminus domain
                containing the cys-x-cys motif of the tissue-preferential
                gene product"

(xi) SEQUENCE DESCRIPTION: SEQ ID NO:10:

Cys Ser Cys Gly Ser Gly Cys Lys Cys Asp Pro Cys Asn Cys
       1               5                   10

(2) INFORMATION FOR SEQ ID NO:11:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..14
            (D) OTHER INFORMATION: /note= "carboxy terminus domain
                containing the cys-x-cys motif of pea metallothionein"

(xi) SEQUENCE DESCRIPTION: SEQ ID NO:11:

Cys Lys Cys Gly Asp Asn Cys Thr Cys Asp Pro Cys Asn Cys
       1               5                   10

(2) INFORMATION FOR SEQ ID NO:12:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:12:

Cys Thr Cys Ala Gly Ser Cys Lys Cys Lys Glu Cys Arg Cys
       1               5                   10

(2) INFORMATION FOR SEQ ID NO:13:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (v) FRAGMENT TYPE: linear (ix) FEATURE:
            (A) NAME/KEY: Peptide
            (B) LOCATION: 1..14
            (D) OTHER INFORMATION: /note= "carboxy terminus domain
                containing the cys-x-cys motif of N. crassa
                metallothionein"

(xi) SEQUENCE DESCRIPTION: SEQ ID NO:13:

Cys Asn Cys Gly Ser Gly Cys Ser Cys Ser Asn Cys Gly Ser
       1               5                   10